(12) United States Patent
Panjabi et al.

(10) Patent No.: US 10,765,819 B2
(45) Date of Patent: Sep. 8, 2020

(54) DOSE COUNTING MECHANISM

(71) Applicants: Akshay Panjabi, Mumbai (IN); Nirmal Panjabi, Mumbai (IN)

(72) Inventors: Akshay Panjabi, Mumbai (IN); Nirmal Panjabi, Mumbai (IN)

(73) Assignee: Newtec Pro Manufacturing Pvt Ltd., Mumbai (IN)

( * ) Notice: Subject to any disclaimer, the term of this patent is extended or adjusted under 35 U.S.C. 154(b) by 842 days.

(21) Appl. No.: 15/328,004

(22) PCT Filed: Jul. 22, 2015

(86) PCT No.: PCT/IB2015/055535
§ 371 (c)(1),
(2) Date: Jan. 20, 2017

(87) PCT Pub. No.: WO2016/012949
PCT Pub. Date: Jan. 28, 2016

(65) Prior Publication Data
US 2017/0157345 A1  Jun. 8, 2017

(30) Foreign Application Priority Data

Jul. 22, 2014  (IN) .......................... 2371/MUM/2014

(51) Int. Cl.
*A61M 15/00* (2006.01)
*G06M 1/24* (2006.01)
(Continued)

(52) U.S. Cl.
CPC ...... *A61M 15/0071* (2014.02); *A61M 15/009* (2013.01); *A61M 15/0068* (2014.02);
(Continued)

(58) Field of Classification Search
CPC ............. A61M 15/00; A61M 15/0001; A61M 15/0021; A61M 15/0065; A61M 15/0068;
(Continued)

(56) References Cited

U.S. PATENT DOCUMENTS 3,931,705 A * 1/1976 Iwaki ..................... G04B 19/21
368/222
5,549,101 A * 8/1996 Trofast .............. A61M 15/0066
128/203.15
(Continued)

FOREIGN PATENT DOCUMENTS

WO   WO-2006062448 A1 *  6/2006  .......... A61M 15/009

*Primary Examiner* — Justine R Yu
*Assistant Examiner* — Matthew D Ziegler

(57) ABSTRACT

A dose counting mechanism for indicating the quantity of dosage available within a metered dose inhaler having a canister with an aerosol fluid and a housing body for housing the canister, wherein a wall of the housing body includes formations to support a resilient element, a wheel formation, a elongate threaded element, and a threaded formation including a pointer. The depressing of the canister to release aerosol fluid displaces the resilient element which engages with the wheel formation to rotate the wheel formation. The elongate threaded element engages with the wheel formation such that the rotation of the wheel formation causes rotational movement of the elongate element. The threaded formation engages with the elongate element whereby the rotational movement of the elongate element causes the linear displacement of the threaded formation and the pointer, whereby the position of the pointer indicates the quantity of fluid within the canister.

10 Claims, 8 Drawing Sheets

(51) Int. Cl.
  *G06M 1/08* (2006.01)
  *G06M 1/04* (2006.01)
(52) U.S. Cl.
  CPC .............. *G06M 1/04* (2013.01); *G06M 1/083* (2013.01); *G06M 1/245* (2013.01)
(58) Field of Classification Search
  CPC ............ A61M 15/007; A61M 15/0071; A61M 15/009; A61M 2210/06; A61M 2210/0625; A61M 15/0073–0078; A61M 2205/60–609; G06M 1/04; G06M 1/045; G06M 1/08; G06M 1/083; G06M 1/22; G06M 1/24; G06M 1/245
  USPC ..... 222/23–51; 116/200, 288, 328; 137/551, 137/556, 556.3
  See application file for complete search history.

(56) References Cited

U.S. PATENT DOCUMENTS

| | | | |
|---|---|---|---|
| 5,871,007 A * | 2/1999 | Clark, Jr. ............ | A61M 15/009 128/200.14 |
| 7,587,988 B2 * | 9/2009 | Bowman .............. | A61M 15/009 116/307 |
| 2004/0231667 A1 * | 11/2004 | Horton ............... | A61M 15/0065 128/202.13 |
| 2014/0150778 A1 * | 6/2014 | Malhotra ........... | A61M 15/0075 128/200.23 |
| 2015/0040890 A1 * | 2/2015 | Besseler ................ | A61M 11/00 128/200.14 |

* cited by examiner

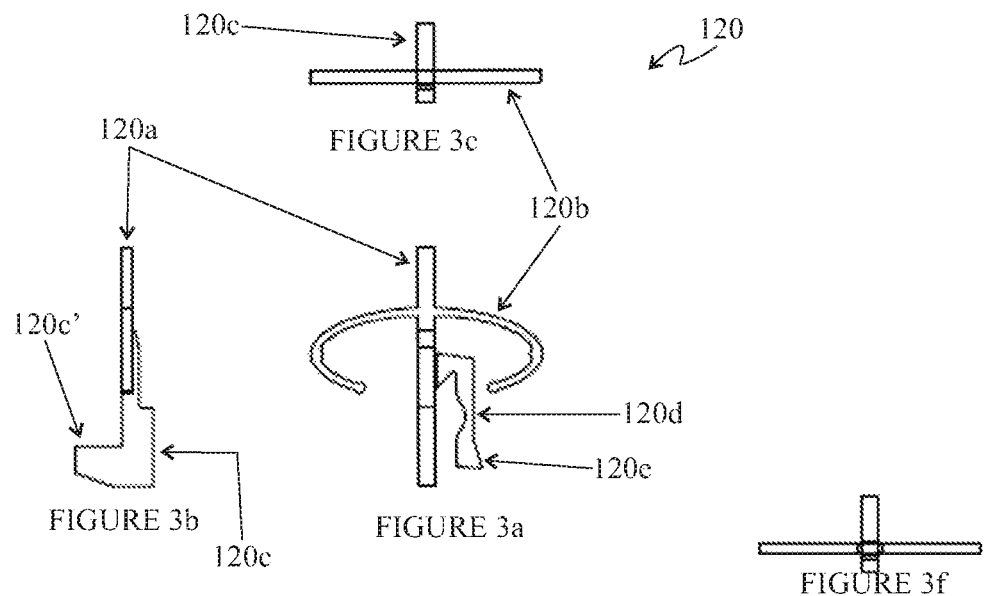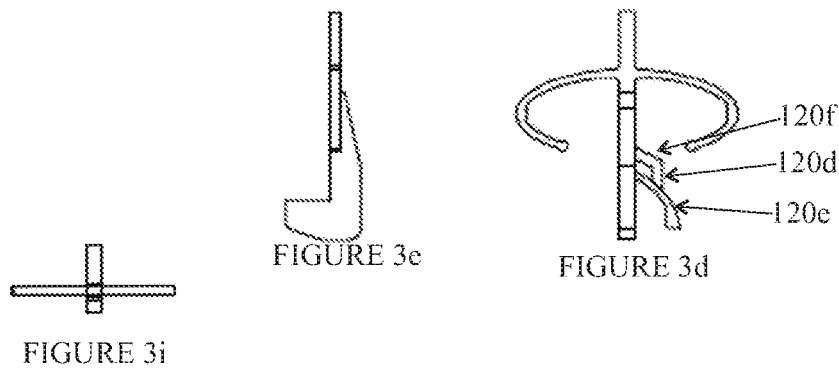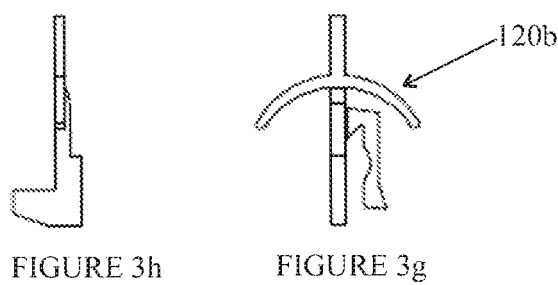

DOSE COUNTING MECHANISM

FIELD OF DISCLOSURE

The present disclosure relates to inhalers used by patients suffering from respiratory disorders. Particularly, the present invention relates to counting and displaying the quantity of medicine/dosage remaining within an inhaler.

Definitions

The term 'pads' used in the context of this disclosure refers to, but is not limited to, flanges extending from a surface.

The term 'inhaler/s' used in the context of this disclosure refers to, but is not limited to, Metered Dose Inhaler/s that are used by patients to self-administer aerosolized medicine via inhalation.

These definitions are in addition to those used in the art.

BACKGROUND

Inhalers are medical devices used for delivering an aerosolized medicine via the throat into the lungs of a patient suffering from respiratory disorders such as chronic obstructive pulmonary disease (COPD), emphysema, bronchitis, asthma, and the like. Inhalers typically include a pressurized canister containing the aerosolized medicine. To release the medicine a user/patient places the inhaler in his/her mouth and depresses the canister that moves intermittently to dispense a discrete amount of the medicine in aerosol form from the inhaler. The medicine is inhaled in the lungs and reaches different airways in the lungs to provide relief to the patient. Patients suffering from chronic respiratory disorders keep such inhaler with them all the time and regularly use the inhaler whenever they face difficulty in breathing which can occur when they are in crowded places, while travelling in crowded vehicles, on dusty roads, and the like. Regular use of the inhaler can lead to fast consumption of the medicine within the canister, whereby unavailability of the medicine in the inhaler at any time when a patient suffers from breathing difficulty or an asthma attack can lead to disastrous consequences for the patient.

Hence, it is imperative for a regular user/patient of the inhaler to know the amount of medicine remaining within the canister of the inhaler. To address this requirement about the amount of medicine left in the inhaler, inhalers with counting means were devised to indicate the amount of medicine remaining in the inhaler generally over a scale.

Indian Patent IN231955 mentions a mechanical counter for a metering apparatus for metering for a medicament. The mechanical counter consists of a spindle with rotary locking, whose axis extends in parallel relationship with the axis of the metering apparatus and which is disposed in the region of the peripheral surface of the apparatus. The spindle is automatically driven by way of a transmission assembly when the metering apparatus is actuated. The number of metering portions already discharged and the number of metering portions permitted in total is quasi-continuously displayed by the mechanical counter. However, such rotary counters consist of a large number of components which make the counter complex and easily susceptible to metering errors and malfunctioning.

The devices in the prior art generally employ complex counting mechanisms which are prone to metering errors due to improper handling. Hence, there is a need for metered dose inhaler having a counting mechanism that accurately counts and indicates precise quantity of medicine remaining in the inhaler.

OBJECTS

Some of the objects of the present disclosure, aimed to ameliorate one or more problems of the prior art or at least provide a useful alternative, are listed herein below.

An object of the present disclosure is to provide a dose counting mechanism that accurately counts the dosages of medicine available within an inhaler.

Another object of the present disclosure is to provide a dose counting mechanism that indicates gross and precise dosages of medicine available within an inhaler.

Another object of the present disclosure is to provide a dose counting mechanism that includes a simple counting mechanism that is free from counting errors.

Another object of the present disclosure is to provide a dose counting mechanism that can be used with a variety of canisters, valves and formulations.

Another object of the present disclosure is to provide a dose counting mechanism that can be used in a metered dose inhaler.

Other objects and advantages of the present disclosure will be more apparent from the following description which is not intended to limit the scope of the present disclosure.

SUMMARY

In accordance with an aspect of the present disclosure, there is provided a dose counting mechanism for indicating the quantity of dosage available within an inhaler, the inhaler having a canister with an aerosol fluid therein and an actuator including a housing body with an elongate cavity for housing the canister therein, the housing body having a top end and a bottom end and defining a vertical axis therethrough, the housing body including a mouth piece extending from the bottom end, a stem extending axially from the mouth piece into the housing body, the stem having a sump defined therein and a passage with an orifice defined therethrough such that the stem and the sump are configured to receive a spring loaded valve of the aerosol loaded canister and to dispense a pre-measured dose of aerosol via the stem and the orifice into the mouth of a user; characterized in that:
  a wall of the housing body comprises,
    an outer surface defining a slit opening within the elongate cavity of the housing body,
    a pair of pads formed on the outer surface of the wall on either side of the slit and above the slit,
    a rail formation, a first guide bracket and a second guide bracket formed on the outer surface of the wall;
  the dose counting mechanism comprises:
    a resilient element defined by:
      a central elongate member,
      resiliently displaceable arms extending on either side of the central elongate member,
      a key member configured at the bottom of the central elongate member, a first nose integral with the key member extending operatively inwardly from one side of the central elongate member, wherein in an operative configuration of the dose counting mechanism, the first nose extends through the slit into the elongate cavity of the housing body and engages with the head of the canister to be displaced within the slit in the event that the canister is depressed by the user, an upper end of the central elongate member slides in the second guide bracket, the ends of the resiliently displaceable arms resiliently deform and slide on the pads; and a pusher configured below one of the arms and extending from the central elongate member, the pusher having a second pushing nose;

a wheel formation having a ratchet wheel formation surrounding an axle integral to the wheel formation on one operative side and a first bevel gear formation on the other operative side, such that in the operative configuration of the dose counting mechanism the wheel formation is positioned on the outer surface of the wall with the ratchet wheel proximal to the outer surface of the wall and the first bevel gear distal from the outer surface of the wall, the second pushing nose engages the ratchet wheel to angularly displace the ratchet wheel tooth by tooth in one direction, wherein a mechanism engages the ratchet wheel to prevent the reverse movement of the ratchet wheel;

an elongate threaded element having a second bevel gear formation extending from an operative lower end of the elongate threaded element and configured to engage the first bevel gear in the operative configuration of the dose counting mechanism, wherein the gear ratio between the first and second bevel gears is such that the movement of one tooth of the ratchet wheel angularly displaces both the first and second bevel gears by one tooth each, thereby causing rotational movement of the elongate threaded element by one pitch;

a threaded formation configured to engage with the threads of the elongate threaded element, and a pointer extending from the threaded formation, the threaded formation being displaceable along the elongate threaded element in response to the rotational movement of the elongate threaded element; and a first cover element is press fitted on the wall to secure the arrangement of the dose counting mechanism thereon, and a second cover element is press fitted on the wall over the first cover element.

Typically, the mechanism engaging the ratchet wheel to prevent the reverse movement of the ratchet wheel, comprises a pawl angularly extending from the first guide bracket and below the first guide bracket in a cavity angularly formed beneath the first guide bracket.

Typically, the wall is a front wall of the housing body.

Additionally, the wall further comprises a through-hole for accommodating the axle of the wheel formation.

Additionally, the wall further comprises a plurality of fixtures for press fittingly locking the second cover thereon.

Typically, the resiliently displaceable arms are either elliptical shaped or bow shaped.

Typically, the pusher is curvilinear.

Additionally, the first cover element comprises:

an aperture for accommodating the second bevel gear and to prevent lateral pressure being exerted on the second bevel gear;

a protrusion at a location corresponding to the center of the wheel formation to firmly hold the wheel formation in place when the first cover is press fitted and prevent the wheel formation from getting dislodged when the ratchet wheel is displaced by the second pushing nose; and a resilient element support formation to support the movement of the central elongate member and the pusher.

Generally, the first cover element is transparent and the second cover element includes a window to view the movement of the pointer and a linear scale adjacent to the window to indicate number of doses of aerosol fluid available in the canister corresponding to a position of the pointer.

Generally, the length of the second cover element is adapted to complement the length of different sizes of canisters.

BRIEF DESCRIPTION OF ACCOMPANYING DRAWINGS

The present disclosure will now be elaborated with the help of the accompanying drawings, in which:

FIG. 1b illustrates an isometric view of the inhaler of FIG. 1a;

FIG. 1c illustrates a back view of the inhaler of FIG. 1a;

FIGS. 3a, 3b and 3c illustrate a front view, a side view and a top view respectively, of an element of the dose counting mechanism comprised within the inhaler of FIG. 1a;

FIGS. 3d, 3e and 3f illustrate a front view, a side view and a top view respectively, of another embodiment of the element illustrated FIGS. 3a, 3b and 3c of the dose counting mechanism comprised within the inhaler of FIG. 1a;

FIGS. 3g, 3h and 3i illustrate a front view, a side view and a top view respectively, of yet another embodiment of the element illustrated FIGS. 3a, 3b and 3c of the dose counting mechanism comprised within the inhaler of FIG. 1a;

FIGS. 4a and 4b illustrate perspective views of another element of the dose counting mechanism comprised within the inhaler of FIG. 1a;

FIG. 4c illustrates a perspective view of yet another element of the dose counting mechanism comprised within the inhaler of FIG. 1a;

FIGS. 4d and 4e illustrate perspective views of still another element of the dose counting mechanism comprised within the inhaler of FIG. 1a;

DETAILED DESCRIPTION

Inhalers used by patients suffering from respiratory disorders contain a specified dosage of medicine therein. Regular use of an inhaler by a patient/user results in fast consumption of the medicine. Hence, it is necessary for a patient/user to keep a track of the amount of dosage available within an inhaler to ensure that the medicine is available to him/her when desired. There have been several endeavors to create inhalers having mechanisms to indicate the dosage available in the inhalers. However, such inhalers consist of complex counting mechanisms that are prone to metering errors and are unreliable.

Hence to overcome the aforementioned problems with inhalers, the present disclosure envisages a dose counting mechanism for accurately counting and indicating the quantity of dosage/medicine available in an inhaler used by patients suffering from respiratory disorders.

The dose counting mechanism of the present disclosure will now be described with reference to the embodiments shown in the accompanying drawings. The embodiments do not limit the scope and ambit of the disclosure. The description relates purely to the examples and preferred embodiments of the disclosed method and its suggested applications.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1A:
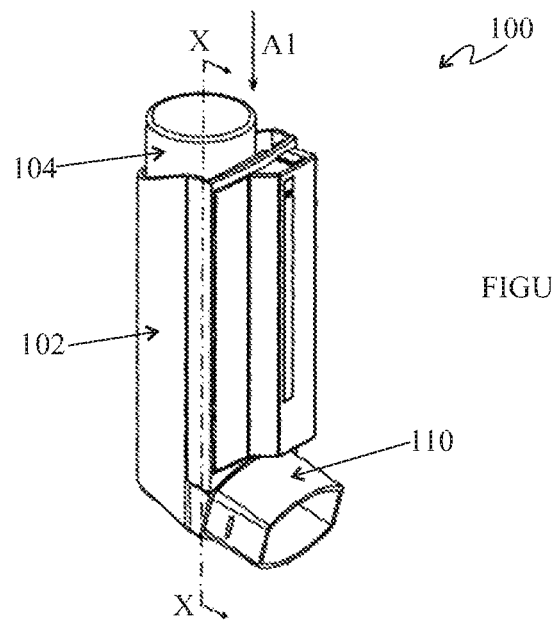
FIG. 1a illustrates a front perspective view of an assembled inhaler comprising a dose counting mechanism in accordance with the present disclosure.
Figure 1B:
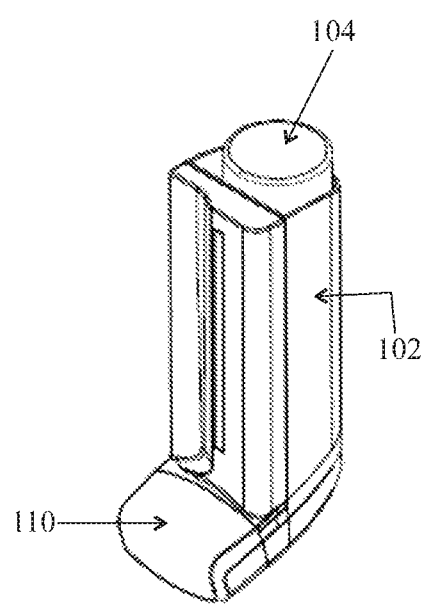
Figure 1C:
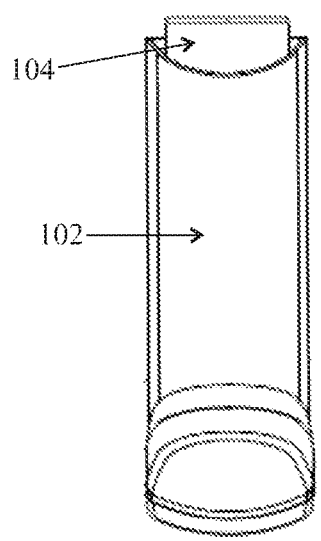

Referring to FIGS. 1a, 1b and 1c, respectively, a front perspective view of an assembled inhaler, an isometric view of the inhaler and a back view of the inhaler, comprising a dose counting mechanism in accordance with the present disclosure is illustrated. The inhaler (100) comprises an actuator including a housing body (102) with an elongate cavity for housing a pressurized canister (104) containing an aerosol fluid. The housing body has a top end and a bottom end defining a vertical axis therethrough, generally referred to as X-axis. The housing body (102) includes a mouth piece (110) angularly extending from the bottom end such that the axis of the mouth piece (110) is inclined at an angle to the axis of the housing body. Generally the axis of the mouth piece (110) is inclined to the axis of the housing body at an angle in the range of 100 degrees to 110 degrees, and typically at an angle of 105 degrees. A stem (110a) extends axially from the mouth piece (110) into the housing body (102). The stem (110a) includes a sump defined therein and a passage with an orifice defined therethrough. The canister (104) is typically a pressurized canister (104) comprising a spring loaded valve (not particularly shown) secured within the canister head (not particularly shown). The canister (104) is longitudinally positioned within the housing body (102) cavity such that the stem (110a) and the sump receive the spring loaded valve of the aerosol loaded canister (104), while a base portion of the canister juts out from the housing body (102). In order to dispense the medicine from the canister (104), a user/patient places the mouth piece (110) into his/her mouth and axially depresses the canister (104) at the bottom of the base portion in the direction indicated by A1, whereupon a pre-measured dose of aerosol is dispensed via the stem (110a) and the orifice into the mouth and the throat of the user to be delivered to the lungs of the user. The housing body (102) further comprises a flat front wall above the mouth piece (110) and a semicircular back portion.

Figure 2:
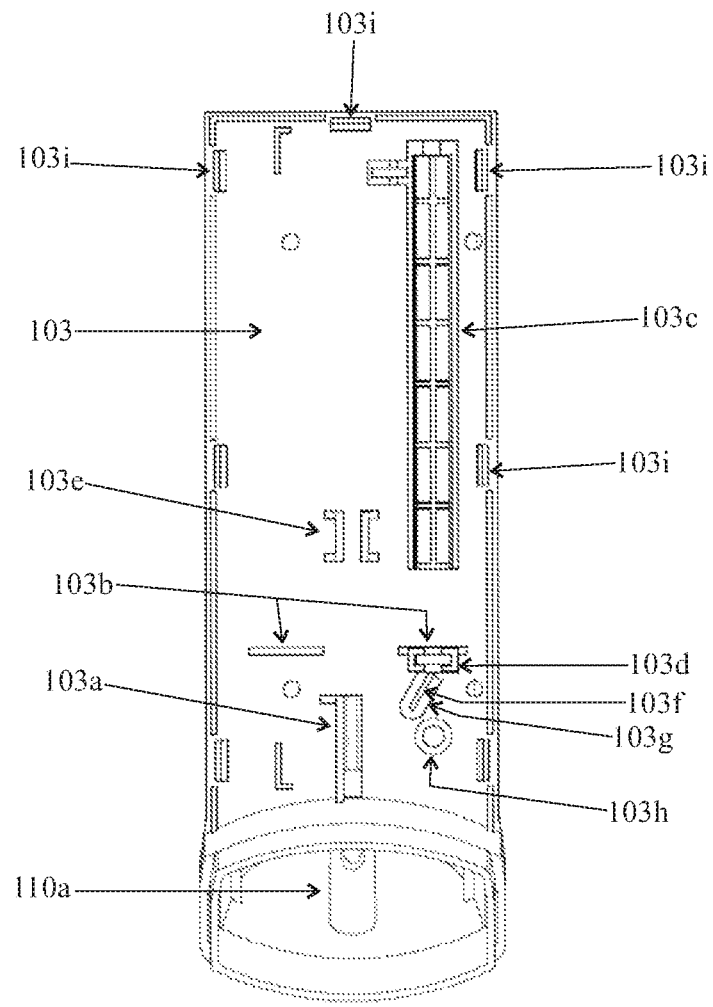
FIG. 2 illustrates a perspective view of the features of the dose counting mechanism comprised within the inhaler of FIG. 1a in an unassembled state.
Figure 4A:
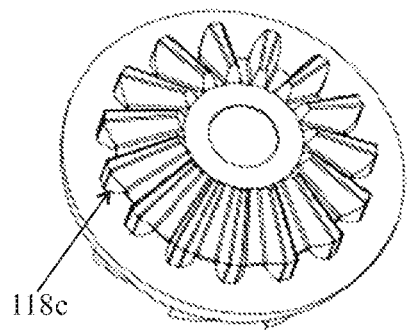
Figure 4B:
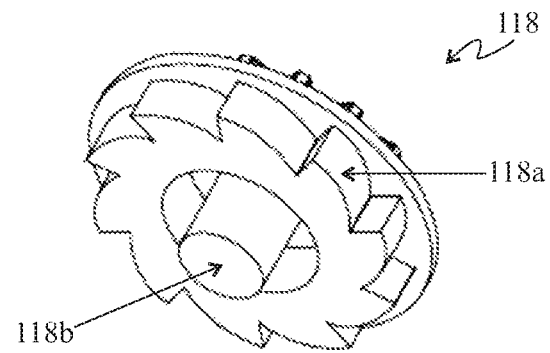
Figure 4C:
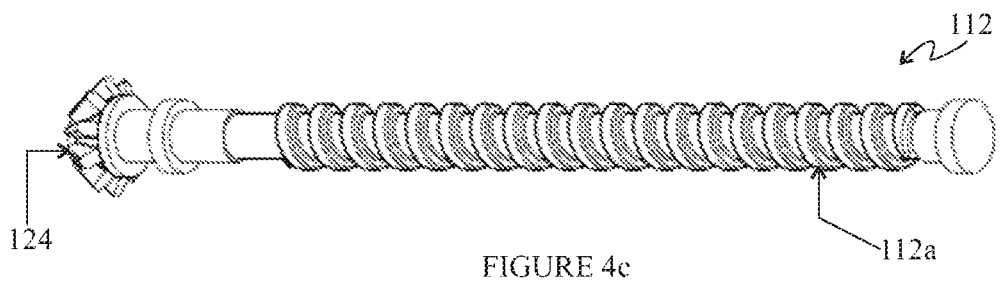
Figure 4D:
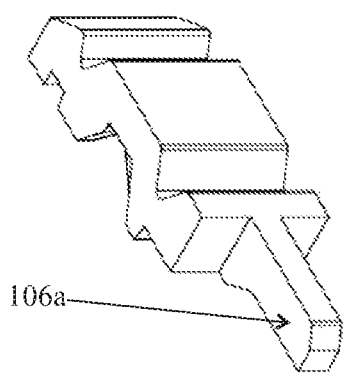
Figure 4E:
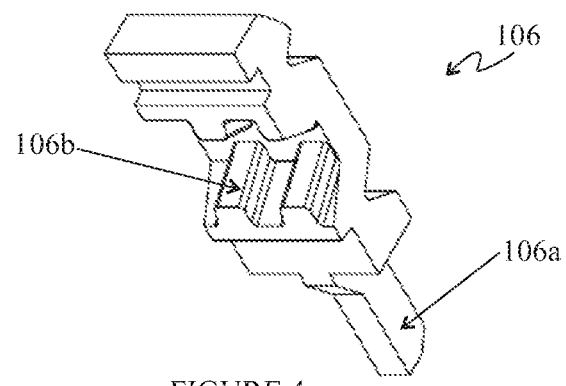

Referring to FIG. 2, a perspective view of the features of the dose counting mechanism comprised within the inhaler of FIG. 1a in an unassembled state is illustrated. The features are moulded on a wall (103) of the housing body (102) of the inhaler. Typically, the wall is a front wall (103) of the housing body. The outer surface of front wall (103) of the housing body (102) comprises a flat plane defining a slit (103a) opening within the housing body (102) cavity, a pair of pads (103b), a rail formation (103c), a first guide bracket (103d), a second guide bracket (103e), a mechanism (103f), a through-hole (103h) and a plurality of fixtures (103i). The pair of pads (103b) are formed on the wall (103) on either said of the slit (103a) and above the slit. The rail formation (103c), a first guide bracket (103d) and a second guide bracket (103e) are formed on the wall (103) at locations to support the different elements of the dose counting mechanism. The mechanism (103f) is typically a pawl (103f) that angularly extends from the first guide bracket (103d) and below the first guide bracket (103d) in a cavity (103g) angularly formed beneath the first guide bracket (103d).

Referring to FIGS. 3a, 3b and 3c, a front view, a side view and a top view respectively, of an element of the dose counting mechanism comprised within the inhaler of FIG. 1a are illustrated. The element (120) has resilient elastic properties and is typically made of polyacetal. The resilient element (120) is defined by a central elongate member (120a), resiliently displaceable elliptical shaped arms (120b), a key member (120c) including an integral first nose (120c'), and a pusher (120d) with a second pushing nose (120e). The elliptical shaped arms (120b) are elastically deformable and extend on either side of the central elongate member (120a). The key member (120c) is integral with the central elongate member (120a). The key member (120c) is configured at the bottom of the central elongate member (120a) and the integral first nose (120c') extends operatively inwardly from one side of the central elongate member (120a). In accordance with one embodiment, the first nose (120c') of the key member (120c) extends perpendicularly from one side of the central elongate member (120a), The pusher arm (120d) is configured below one of the resiliently displaceable elliptical shaped arms (120b) and extends from a side of the central elongate member (120a).

Referring to FIGS. 3d, 3e and 3f a front view, a side view and a top view respectively, of another embodiment of the element (120) illustrated FIGS. 3a, 3b and 3c of the dose counting mechanism comprised within the inhaler of FIG. 1a is illustrated. In the embodiment of the resilient element (120) illustrated in FIGS. 3d, 3e, and 3f, the pusher (120d) with the second pushing nose (120e) is curvilinear shaped, shorter in length, configured below one of the resiliently displaceable elliptical shaped arms (120b) and extends angularly from the central elongate member (120a). Additionally, a support arm (120f) is integrally placed between the central elongate member (120a) and the pusher (120d), to prevent reverse movement and cause damping of the pusher (120d) when displaced due to the displacement of the resilient element (120).

Referring to FIGS. 3g, 3h and 3i a front view, a side view and a top view respectively, of yet another embodiment of the element (120) illustrated FIGS. 3a, 3b and 3c of the dose counting mechanism comprised within the inhaler of FIG. 1a is illustrated. In the embodiment of the resilient element (120) illustrated in FIGS. 3g, 3h, and 3i, the resilient element (120) comprises resiliently displaceable bow shaped arms (120b) extending on either side of the central elongate member (120a).

Figure 6:
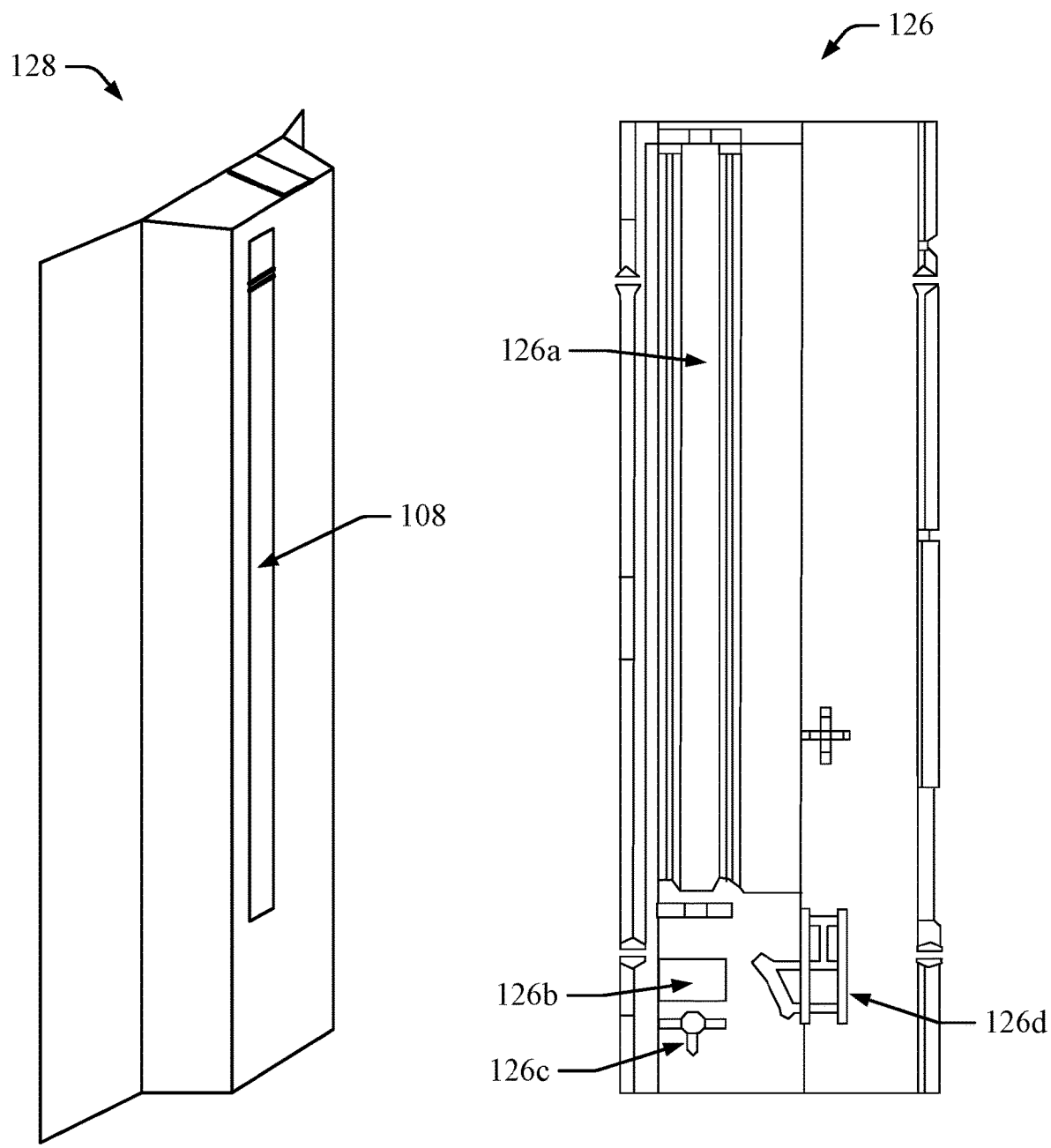
FIG. 6 illustrates a perspective view of the features of another element of the dose counting mechanism comprised within the inhaler of FIG. 1a in an unassembled state.

Referring to FIGS. 4a-4e, perspective views of more elements of the dose counting mechanism comprised within the inhaler of FIG. 1a are illustrated. The dose counting mechanism further comprises a wheel formation (118) having a ratchet wheel (118a) formation surrounding an axle (118b) integral to the wheel formation (118) on one operative side and a first bevel gear (118c) on the other operative side, an elongate threaded element (112) having a plurality of helical threads (112a) formed thereon and a second bevel gear (124) extending from an operative lower end of the elongate threaded element (112), a threaded formation (106) having a pointer (106a) extending therefrom and threads (106b) formed on an operative back side of said threaded formation (106), a first cover element (126) (as shown in FIG. 6) press fittable on the wall (103) to secure the resilient element (120), the wheel formation (118), the elongate threaded element (112) and the threaded formation (106) on the wall, and a second cover element (128) (as shown in FIG. 6) with a window (108) press fittable on the wall (103) over the first cover element (126). The through-hole (103h) in the front wall (103) receives the axle (118b) therein. In accordance with one embodiment, the axle (118b) is positioned at the central axis of the wheel formation (118). In accordance with another embodiment, the axle (118b) is positioned to cause eccentric rotation of the wheel formation (118b).

Figure 5A:
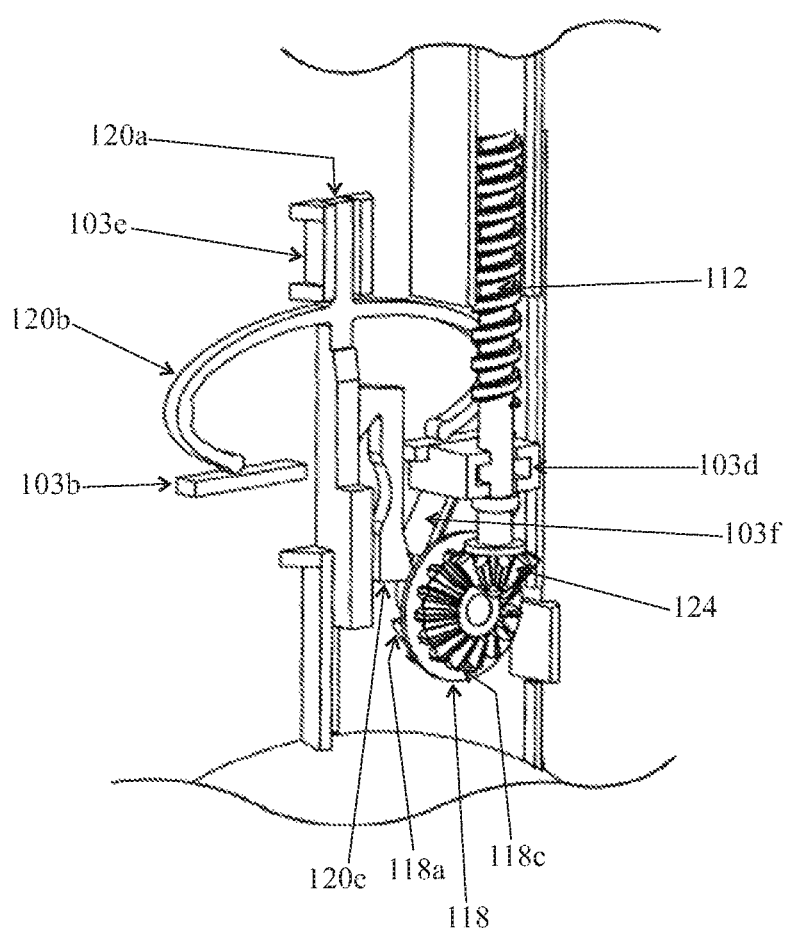
FIG. 5a illustrates an assembled operative configuration of the dose counting mechanism comprised within the inhaler of FIG. 1a, wherein the dose counting mechanism comprises the element illustrated FIGS. 3a, 3b and 3c.
Figure 5B:
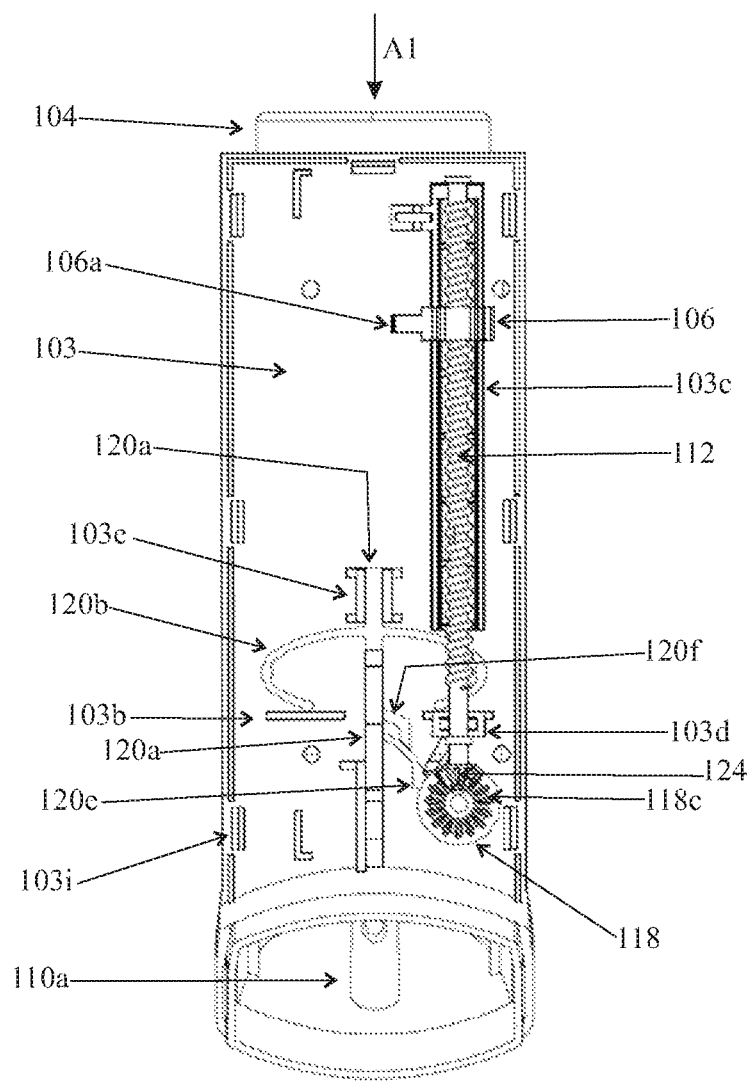
FIG. 5b illustrates an assembled operative configuration of the dose counting mechanism comprised within the inhaler of FIG. 1a, wherein the dose counting mechanism comprises the element illustrated FIGS. 3d, 3e and 3f.

Referring to FIG. 5a an operative configuration of the assembled dose counting mechanism comprised within the inhaler of FIG. 1a is illustrated, wherein the dose counting mechanism comprises the element illustrated FIGS. 3a, 3b and 3c. In accordance with the operative configuration of the dose counting mechanism, the operatively inwardly extending first nose (120c') of the key member (120c) extends through the slit (103a) into the elongate cavity of the housing body (102) and engages with the head of the canister (104), the wheel formation (118) is positioned on the outer surface of the wall (103) with the ratchet wheel (118a) proximal to the outer surface of the wall (103) and the first bevel gear (118c) distal from the outer surface of the wall (103). In the event that the user axially depresses the canister (104) at the bottom of the base portion in the direction indicated by A1, the head of the canister (104) engaging the first nose (120c') of the key member (120c) causes the key member (120c) to slide down within the slit (103a) along with the displacement of the canister in the housing (102) cavity, thereby causing displacement of the resilient element (120). The upper end of the central elongate member (120a) slides in the second guide bracket (103e), and the ends of the flexible elliptical shaped arms (120b) slide on the pads (103b). The second pushing nose (120e) engages the ratchet wheel (118a) to angularly displace the ratchet wheel (118a) by one tooth at a time. The second bevel gear (124) engages with the first bevel gear (118c), wherein the gear ratio between the first (118c) and second (124) bevel gear is such that the movement of one tooth of the ratchet wheel (118a) angularly displaces both the first (118c) and second (124) bevel gears by one tooth each, thereby causing rotational movement of the elongate threaded element (112). The threads (106b) of the threaded formation (106) engage with the helical threads (112a) of the elongate threaded element (112), causing the threaded formation (106) and thereby the pointer (106a) to displace down along the elongate element (112) in response to the rotational movement of the elongate element (112) (as shown in FIG. 5b), thereby counting down the dosage available in the canister (104) by one count. Each such depression of the canister (104) causes decrease of the dosage available in the canister (104) by one count. A precise number of teeth are formed on the ratchet wheel (118a), the first bevel gear (118c) and the second bevel gear (124) and a precise number of helical threads are formed on the elongate threaded element (112) to count down a specific number of doses. In accordance with one embodiment, the number of doses to be counted down is 200 doses; in accordance with another embodiment, the number of doses to be counted down is 120 doses; and so on.

After the aerosol fluid is dispensed from the canister, the spring loaded valve in the canister (104) relaxes causing the canister to move back to its original position. The resilient elastic properties of the flexible elliptical shaped arms (120b) results in resetting motion of the elliptical shaped arms (120b) causing the elliptical shaped arms (120b) to move upwards, whereby the key member (120c) slides back up in the slit (103a) and the ends of the elliptical shaped arms (120b) slide back on the pads (103b) and come to rest and are ready for subsequent use with release of next dosage. The pusher (120d) also moves upwards against the ratchet wheel (118a) on the wheel formation (118). However, the reverse movement of the ratchet wheel (118a) and the wheel formation (118) is restricted by the pawl (103f).

Referring to FIG. 5b an assembled operative configuration of the dose counting mechanism comprised within the inhaler of FIG. 1a is illustrated, wherein the dose counting mechanism comprises the element illustrated FIGS. 3d, 3e and 3f. In the operative configuration, the support arm (120f) causes damping of the push arm (120d) due to the opposing force from the tooth of the ratchet wheel (118a), when the second pushing nose (120e) engages the tooth of the ratchet wheel (118a) to displace the ratchet wheel (118a) upon displacement of the resilient element (120).

Figure 5C:
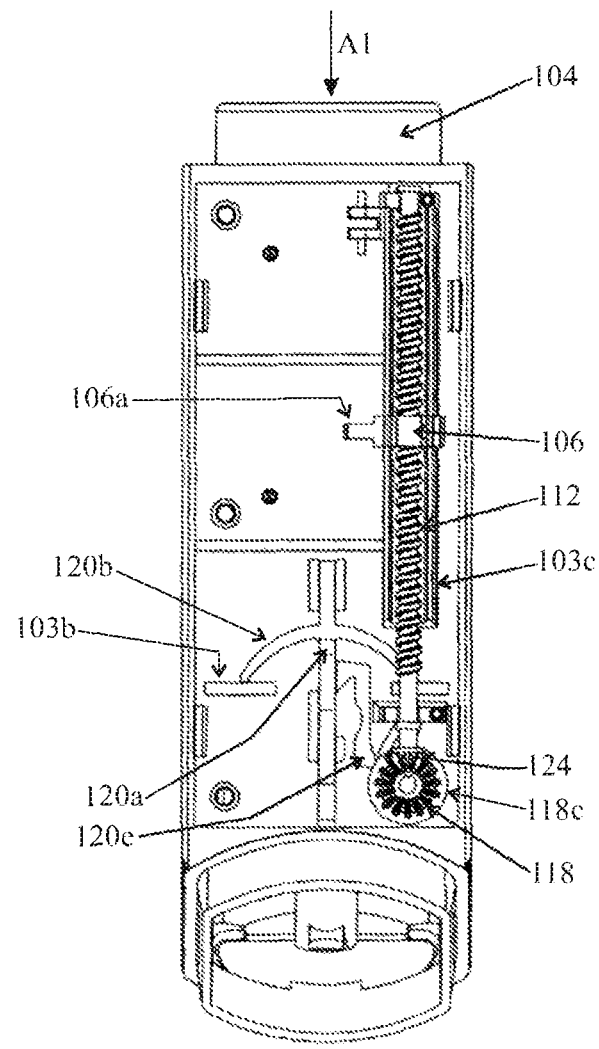
FIG. 5c illustrates an assembled operative configuration of the dose counting mechanism comprised within the inhaler of FIG. 1a, wherein the dose counting mechanism comprises the element illustrated FIGS. 3g, 3h and 3i.

Referring to FIG. 5c an assembled operative configuration of the dose counting mechanism comprised within the inhaler of FIG. 1a is illustrated, wherein the dose counting mechanism comprises the element illustrated FIGS. 3g, 3h and 3i. The bow shaped arms (120b) are elastically deformable. In the operative configuration of the inhaler dose counter, the bow shaped arms (120b) slide and come to rest on the pads (103b).

Referring to FIG. 6, a perspective view of the features of another element of the dose counting mechanism comprised within the inhaler of FIG. 1a in an unassembled state is illustrated. The element illustrated in FIG. 6 is the first cover element (126) which is press fitted on the wall (103) to secure the resilient element (120), the wheel formation (118), the elongate threaded element (112) and the threaded formation (106) on the wall. The first cover element (126) comprises a rail formation (126a), an aperture (126b), a protrusion (126c), and a resilient element support formation (126d). The rail formation (126a) supports the movement of the threaded formation (106) along the threads of the linear bolt (112). The aperture (126b) accommodates the second bevel gear (124) and prevents lateral pressure being exerted on the second bevel gear (124) while the second bevel gear is rotated by the first bevel gear (118c). The location of the protrusion (126c) corresponds to the center of the wheel formation (118) to firmly hold the wheel formation in place when the first cover element is press fitted and prevent the wheel formation (118) from getting dislodged when the ratchet wheel (118a) is displaced by the second pushing nose (120e). The resilient element support formation (126d) supports the movement of the central elongate member (120a) and the push arm (120d). In accordance with one embodiment, the first cover element (126) is transparent.

The second cover element (128) of the dose counting mechanism is press fitted on the wall (103) over the first cover element (126). The fixtures (103i) on the wall (103) press fittingly receive the second cover element (128). The second cover element (128) includes a window (108) to view the pointer (106a) movement and a scale adjacent the window (108) to indicate a quantity of aerosol fluid available in the canister corresponding to a position of the pointer (106a). In accordance with one embodiment, the scale is printed adjacent the window (108). In accordance with another embodiment, the scale is in the form of a sticker pasted adjacent the window (108). In accordance with yet another embodiment, the scale is engraved adjacent the window (108). In accordance with still another embodiment, the scale is embossed adjacent the window (108). As described herein above, threaded formation (106) and thereby the pointer (106a) travels from the top of the window (108) to the bottom of window (108) with the usage of the inhaler (100). With every single use threaded formation (106) and thereby the pointer (106a) travels down by a predefined distance indicating the quantity of aerosol fluid remaining in the inhaler on the scale. A bottom position of the pointer (106a) indicates that the medicine in the inhaler is exhausted. Typically, the scale includes color variations to indicate different quantity of dosage available in the canister (104). In accordance with one embodiment, the pointer (106a) is in the form of a magnifying glass with a meniscus. In accordance with another embodiment, the pointer (106a) is composed of luminescent materials causing the pointer to glow in dark and enabling user to view the quantity of dosage available even in no light conditions. In accordance with yet another embodiment, an LED is provided between the cover elements and the wall (103) and a button connected to the LED is provided on the housing body (102) to illuminate the LED to enable users to view the pointer.

Typically, the second cover element (128) is sized such that the length of the second cover element (128) complements the length of the elongate bodies of different sizes of canisters.

Thus, the combination of the wall (103) with the specially moulded formations (103a-103i), the resilient element (120), the wheel formation (118), the elongate threaded element (112), the threaded formation (106), the first cover element (126) and the second cover element (128) provide a dose counting mechanism with a simple mechanism that is error free and accurately counts and indicates the quantity of dosage available in an inhaler, enabling the inhaler to be conveniently used by patients suffering from respiratory disorders.

Technical Advancements and Economic Significance

The technical advancements offered by the dose counting mechanism of the present disclosure include the realization of:
- accurate counting of the quantity of medicine available within an inhaler;
- indicating a precise quantity of medicine available within an inhaler;
- a simple counting mechanism that is free from counting errors; and
- usability with a variety of canisters, valves and formulations.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A dose counting mechanism for indicating the quantity of dosage available within an inhaler, the inhaler having a canister with an aerosol fluid therein and an actuator including a housing body with an elongate cavity for housing the canister therein, the housing body having a top end and a bottom end and defining a vertical axis therethrough, the housing body including a mouth piece extending from the bottom end, a stem extending axially from the mouth piece into the housing body, the stem having a sump defined therein and a passage with an orifice defined therethrough such that the stem and the sump are configured to receive a spring loaded valve of the aerosol loaded canister and to dispense a pre-measured dose of aerosol via the stem and the orifice into a mouth of a user, the dose counting mechanism comprising:
   a wall of the housing body further comprising,
      an outer surface defining a slit opening within the elongate cavity of the housing body,
      a pair of pads formed on the outer surface of the wall on either side of the slit opening and above the slit opening,
      a rail formation, a first guide bracket and a second guide bracket formed on the outer surface of the wall;
   said dose counting mechanism further comprising:
      a central elongate member,
      a resilient element defined by:
         resiliently displaceable arms extending on either side of the central elongate member,
         a key member configured at the bottom of said central elongate member, a first nose integral with said key member extending operatively inwardly from one side of said central elongate member, wherein in an operative configuration of said dose counting mechanism, said first nose extends through said slit opening into the elongate cavity of the housing body and engages with a head of the canister to be displaced within said slit opening in an event that the canister is depressed by the user, an upper end of said central elongate member slides in said second guide bracket, and ends of said resiliently displaceable arms resiliently deform and slide on said pads; and a pusher configured below one of said arms and extending from said central elongate member, said pusher having a second pushing nose;

a wheel formation with a first operative side and a second operative side having a ratchet wheel formation surrounding an axle integral to said wheel formation on the first operative side and a first bevel gear formation on the second operative side, such that in the operative configuration of said dose counting mechanism said wheel formation is positioned on the outer surface of said wall with said ratchet wheel proximal to the outer surface of the wall and said first bevel gear distal from the outer surface of said wall, said second pushing nose engages said ratchet wheel to angularly displace said ratchet wheel tooth by tooth in one direction, wherein a pawl mechanism engages said ratchet wheel to prevent a reverse movement of said ratchet wheel;

an elongate threaded element having a second bevel gear formation extending from an operative lower end of said elongate threaded element and configured to engage said first bevel gear in the operative configuration of said dose counting mechanism, wherein the gear ratio between said first and second bevel gears is such that a movement of one tooth of said ratchet wheel angularly displaces both said first and second bevel gears by one tooth each, thereby causing rotational movement of said elongate threaded element by one pitch;

a threaded formation configured to engage with the threads of said elongate threaded element, and a pointer extending from said threaded formation, said threaded formation being displaceable along said elongate threaded element in response to the rotational movement of said elongate threaded element; and a first cover element is press fitted on said wall to secure the arrangement of said dose counting mechanism thereon, and a second cover element is press fitted on said wall over said first cover element.

2. The dose counting mechanism as claimed in claim 1, wherein said pawl mechanism engaging said ratchet wheel to prevent the reverse movement of said ratchet wheel, comprises a pawl angularly extending from said first guide bracket and below said first guide bracket in a cavity angularly formed beneath said first guide bracket.

3. The dose counting mechanism as claimed in claim 1, wherein said wall is a front wall of the housing body.

4. The dose counting mechanism as claimed in claim 1, wherein said wall further comprises a through-hole for accommodating said axle of said wheel formation.

5. The dose counting mechanism as claimed in claim 1, wherein said wall further comprises a plurality of fixtures for press fittingly locking said second cover element thereon.

6. The dose counting mechanism as claimed in claimed 1, wherein said resiliently displaceable arms are either elliptical shaped or bow shaped.

7. The dose counting mechanism as claimed in claim 1, wherein said pusher is curvilinear.

8. The dose counting mechanism as claimed in claim 1, wherein said first cover element comprises:

an aperture for accommodating said second bevel gear and to prevent lateral pressure being exerted on said second bevel gear; a protrusion at a location corresponding to the center of said wheel formation to firmly hold said wheel formation in place when said first cover element is press fitted and prevent said wheel formation from getting dislodged when said ratchet wheel is displaced by said second pushing nose; and a resilient element support formation to support a movement of said central elongate member and said pusher.

9. The dose counting mechanism as claimed in claim 1, wherein said first cover element is transparent and said second cover element includes a window to view a movement of said pointer and a linear scale adjacent to said window to indicate number of doses of aerosol fluid available in the canister corresponding to a position of said pointer.

10. The dose counting mechanism as claimed in claim 1, wherein the length of said second cover element is adapted to complement the length of different sizes of canisters.

* * * * *